Figure 1A:
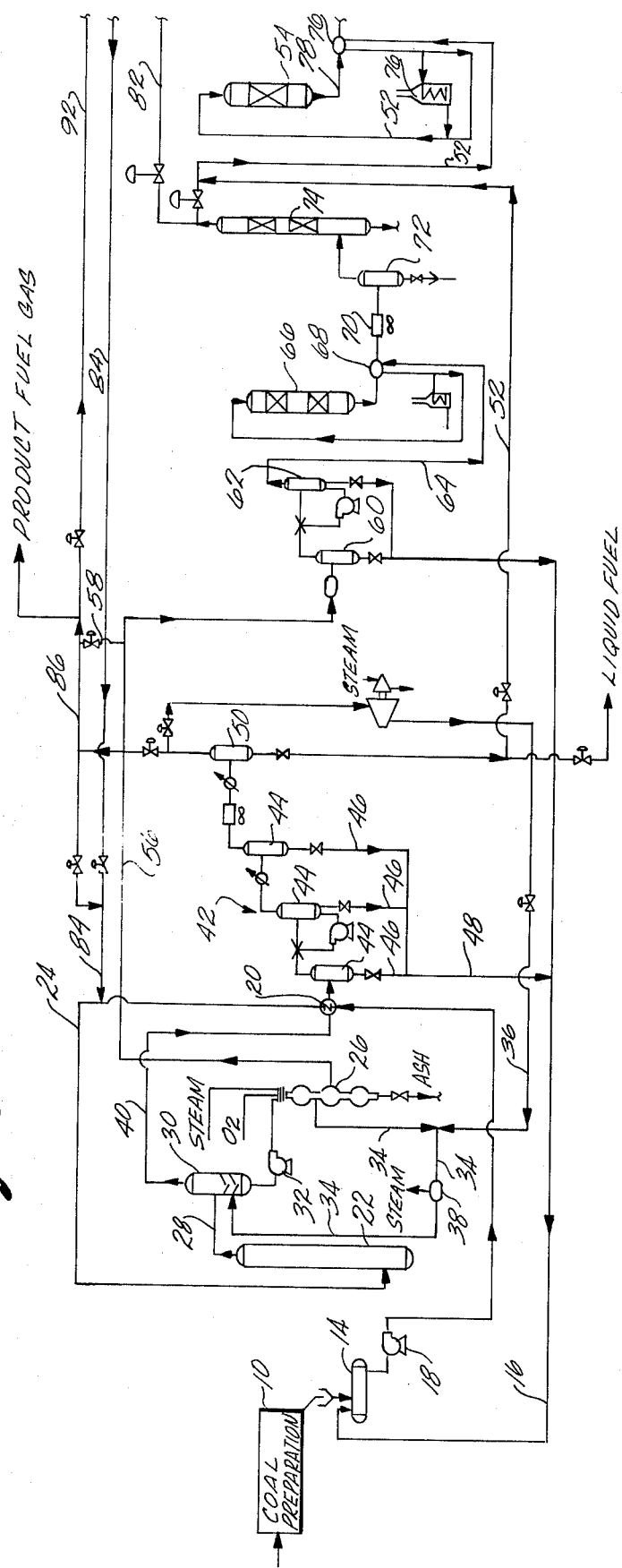

United States Patent [19]

McNamee et al.

[11] 4,050,908

[45] Sept. 27, 1977

[54] PROCESS FOR THE PRODUCTION OF FUEL VALUES FROM COAL

[75] Inventors: Gerald P. McNamee, Santa Ana; Theodore R. Roszkowski, Malibu; David W. Stanbridge, Pacific Palisades; Gerald A. White, Los Angeles, all of Calif.

[73] Assignee: The Ralph M. Parsons Company, Pasadena, Calif.

[21] Appl. No.: 707,004

[22] Filed: July 20, 1976

[51] Int. Cl.$^2$ .......................... C10J 3/16; C10K 3/04
[52] U.S. Cl. .......................................... 48/210; 208/8; 260/449 M
[58] Field of Search ...................... 208/8; 260/449 M; 48/197 R, 206, 210

[56] References Cited

U.S. PATENT DOCUMENTS

| | | | |
|---|---|---|---|
| 3,598,718 | 8/1971 | Glein et al. | 208/8 |
| 3,726,784 | 4/1973 | Correa et al. | 208/8 |
| 3,755,136 | 8/1973 | Fields et al. | 208/8 |
| 3,938,968 | 2/1976 | White et al. | 48/197 R |

Primary Examiner—S. Leon Bashore
Assistant Examiner—Peter F. Kratz
Attorney, Agent, or Firm—Christie, Parker & Hale

[57] ABSTRACT

A slurry of particulate coal and a liquid hydrocarbon solvent formed from liquefaction of coal in the presence of hydrogen are combined with hydrogen in a liquefaction zone operated at temperatures from 700° to 1000° F, and pressures up to about 2500 psi. There are generated vapor and liquid hydrocarbons and solid residue. Light liquid hydrocarbons may be recovered as a product or ultimately converted to methane. Another portion of the liquid is recycled as the hydrocarbon solvent. The higher boiling liquid hydrocarbons and the solid residue are subjected to gasification to yield a synthesis gas which serves as a stripping gas stream used for separating the products of liquefaction into useful constituents. Preferably, all of the synthesis gas formed in the process, hydrocarbon vapor, and the light liquid hydrocarbons are converted by a combination of reforming and methanation operations to methane.

23 Claims, 2 Drawing Figures

PROCESS FOR THE PRODUCTION OF FUEL VALUES FROM COAL

BACKGROUND OF THE INVENTION

Dwindling reserves of liquid fossil fuels have placed greater emphasis on solid carbonaceous materials, especially coal, as a source of energy. An energy source of particular concern is methane, as it is highly desired to convert the available liquid fossil fuels to other products. Attention, therefore, has been strongly focused on processes which are directed to the ultimate conversion of coal into methane.

A need exists for a highly efficient process for the production of methane from coal and one which is sufficiently flexible to provide alternate liquid and gaseous fuel products.

SUMMARY OF THE INVENTION

According to the present invention, there is provided a process for the production of a fuel gas and a liquid fuel from coal, both of which may be ultimately converted to methane.

The basic operation of the present invention follows first forming a slurry of particulate coal in a liquid hydrocarbon solvent predominantly composed of hydrocarbons boiling up to about 750° F, preferably from about 300° to about 750° F, and more preferably from about 500° to about 750° F, and generated as a consequence of liquefying coal in the presence of hydrogen and the liquid hydrocarbon solvent.

The slurry and a hydrogen containing gas are combined in a liquefaction zone and maintained at a temperature from about 700° to about 1000° F, preferably from about 800° to about 900° F, and at a pressure up to about 2500 psi, preferably 1000 to 1500 psi depending upon the effective partial pressure of the hydrogen containing gas. Residence time in the liquefaction zone is sufficient to convert at least a substantial portion of the coal to hydrocarbons which are fluid at the operating temperature and pressure of the liquefaction zone. The products include hydrocarbon vapors, liquid hydrocarbons, and a solid residue of liquefaction.

The effluent from the liquefaction zone is combined with a synthesis gas in a stripping zone. There, the synthesis gas serves to form a vapor fraction comprising hydrocarbons, carbon monoxide, carbon dioxide and hydrogen, and leaves a liquid-solids fraction composed of heavy hydrocarbons boiling above the temperature at which the separation occurs and the solid residue of liquefaction.

The liquid-solids fraction from the stripping zone is combined with steam and oxygen in an amount sufficient to gasify essentially all of the carbon contained in the fraction in a gasification zone to generate a synthesis gas comprising the oxides of carbon and hydrogen. At least a major portion of the synthesis gas is passed to the stripping zone to achieve the separation between the vapor fraction and the liquid-solids fraction.

After being utilized for stripping, the synthesis gas may be recovered with vaporized hydrocarbons containing up to about 5 hydrocarbon atoms as a product fuel gas or a portion utilized for its hydrogen content in the liquefaction zone.

Of the vaporized hydrocarbons from the stripping zone a fraction may be separated as light liquid hydrocarbon fuel comprising hydrocarbons containing more than about 5 carbon atoms to hydrocarbons boiling up to 500° F, preferably up to 300° F and the balance recycled as the hydrocarbon solvent for coal. A product fuel gas and product liquid fuel if recovered, would contain hydrogen sulfide and the product streams would be ultimately treated for its removal. of methane. For its production, a minor portion of the synthesis gas may be converted into a hydrogen rich gas stream for feed to the liquefaction zone and to hydrotreat the light liquid hydrocarbon fraction to eliminate bound sulfur. The pressurized light liquid hydrocarbon is passed to a reforming zone along with a portion of the residual vapor fraction formed as a consequence of the recovery of the light liquid hydrocarbon fraction, which residual vapor fraction is previously stripped of at least a portion of contained carbon dioxide and hydrogen sulfide.

The balance of the carbon dioxide and hydrogen sulfide lean vapor fraction is passed to a first methanation zone containing a supported catalyst containing from about 5 to about 35% by weight of at least one metal of the third period of Group VIII of the Periodic Table on a temperature stabilized ceramic alumina support. In the methanation zone which has an inlet temperature of at least about 900° F and temperatures up to about 1500° F, methane is produced in the presence of steam with generation of exothermic heat. The effluent of the methanation zone is fed to the reforming zone to supply the heat requirements of the endothermic reforming reaction.

The gaseous product resulting from the reforming of the light hydrocarbons and the carbon oxides are passed to at least one additional methanation stage where hydrogen and carbon monoxide react to form additional methane. Preferably, a plurality of methanation stages are employed, each operating under the conditions of the first methanation stage with intermediate removal of heat between each stage.

In a preferred operation, the gas stream after reforming is subject to a stage of catalytic shift reaction where any residual organic sulfides are decomposed and stripped of hydrogen sulfide before passage to the further methanation stage or stages.

In employing the process as described, generally about 80% of the carbon in the coal, exclusive of the carbon present in the hydrocarbon solvent, appears in the feed to be gasified, about 10% as the light liquid hydrocarbon, and about 10% as vaporized hydrocarbons.

THE DRAWINGS

Figure 1B:
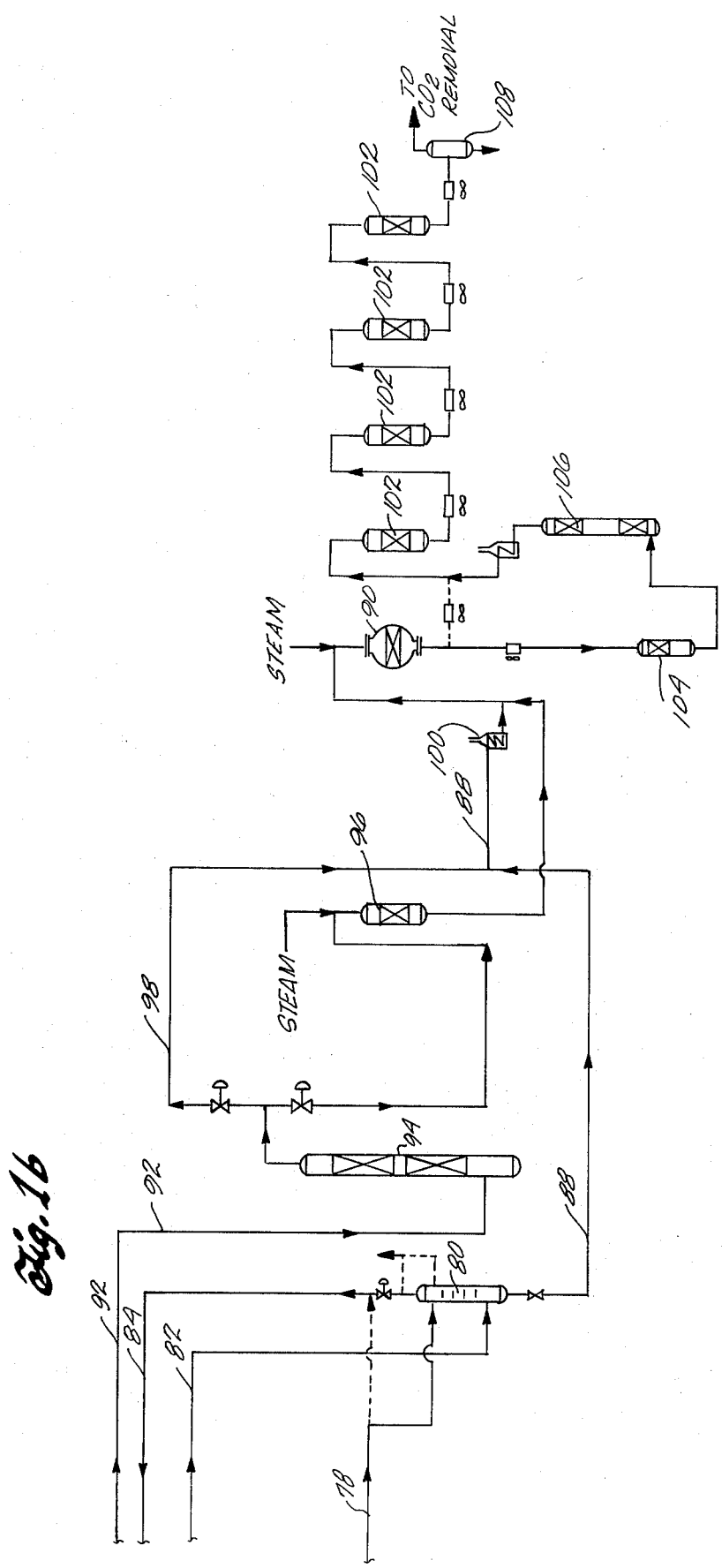

FIGS. 1a and 1b schematically illustrate the process of this invention.

DESCRIPTION

With reference to the Drawings, coal which may be anthracite coal, bituminous coal, sub-bituminous coal, peat, lignite and the like and sulfur bearing is prepared by crushing or grinding operations in a coal preparation unit 10. Typically the coal is ground to a particle size less than about 40 mesh, with a major portion, e.g., about 80% of the particles, being less than about 200 mesh. The coal after comminution may be dried to about a 2% moisture content. The comminuted coal is blended in slurry tank 14 with a liquid hydrocarbon solvent, supplied to slurry tank 14 by line 16 and/or a reservoir (not shown). The liquid hydrocarbon solvent comprises the hydrocarbons having boiling points below about 750° F and generated by liquefaction of the coal in the presence of hydrogen. The preferred liquid hydrocarbon solvent is one comprising hydrocarbons boiling in the range from about 300° to about 750° F, and more preferably in the range from about 500° to about 750° F.

The effluent from the slurry tank 14 is pressured and transferred by pump 18 through heat exchanger 20 in indirect exchange with the vapor effluent of stripper 30 and passed by line 24 to liquefaction zone 22 where in combination with hydrogen. The source of hydrogen may be a portion of the fuel gas resulting from stripping of the effluent of the liquefaction zone with a synthesis gas or a hydrogen rich gas produced from a synthesis gas generated in the process.

Typically the weight ratio of hydrocarbon solvent to coal is from about 1:1 to about 3:1 depending on the effectiveness of the liquid in absorbing the heat of liquefaction. The preferred range is from about 1.5:1 to about 2.5:1

Liquefaction zone or dissolver 22 is operated at an elevated temperature normally in the range from about 700° to about 1000° F, preferably from about 800° to about 900° F, and a high pressure, typically up to about 2500 psi and preferably from about 1000 to about 1500 psi.

The amount of hydrogen supplied to dissolver 22 is normally about 2% by weight of the coal, i.e., about 2 pounds of hydrogen per 100 pounds of coal. Excess hydrogen may be provided to maintain a desired partial pressure of hydrogen in dissolver 22 as well as for control of temperature.

In dissolver 22, the coal in the presence of the liquid hydrocarbon solvent and hydrogen undergoes thermal reactions with accompanying hydrogenation of the product and hydrocracking to yield hydrocarbons having a broad boiling point distribution. The liquid hydrocarbon solvent also serves as a sink to control reaction temperature.

The effluent of dissolver 22 in line 28 is a three phase mixture which includes unutilized constituents of the source of hydrogen, hydrocarbon vapors generated through liquefaction, hydrocarbons which are liquid at the operating conditions in dissolver 22 and solid residue of liquefaction. The mixture passes to stripper 30 operated at essentially the same pressure as dissolver 22. In stripper 30 the dissolver effluent is combined with a gas comprising a major portion if not all of the synthesis gas generated in gasifier 26 from a portion of the products of liquefaction. Normally from about 60 to 100%, more typically from about 80 to about 90%, of the generated synthesis gas serves as stripping gas. The synthesis gas in line 34 may or may not be cooled in steam generator 38 as determined by temperature requirements set by the feed to stripping zone 30. If desired aportion of compressed vapor products from separator 50 may be used to quench the syngas ahead of steam generator 38.

The steam generated as a consequence of cooling of the synthesis gas is at approximately 1500 psi and is used in the process, for example, for driving compressors, or for reforming and methanation. Ash is withdrawn from the base of gasifier 26.

Stripper 30 yields a vapor and a liquid solids stream. Besides the oxides of carbon and hydrogen contained in the stripping gas, the vapor stream comprises hydrocarbons boiling below the normal operating temperature and pressure of stripping zone 30. Typically, hydrocarbons boiling above 750° F are separated in admixture with the solid residue of liquefaction. The lower boiling hydrocarbons remain in the vapor although, as will be understood, an overlap of materials from each fraction formed will appear in the other fraction.

The mixture of liquid and solids is transferred by pump 32 to gasifier 26 where through the addition of steam and oxygen, the carbon present in both the liquids and solids is converted in bulk to a syngas comprising hydrogen and the oxides of carbon at temperatures up to about 2200° to about 2600° F at pressures from about 1200 to about 2500 psig.

At least the bulk of the syngas generated is preferably passed by line 34 for combination with cooled compressed gas in line 36 and typically quenched to a temperature of about 1700° F and cooled in steam generator 38 to from about 700° to about 1000° F for feed to stripper 30. The balance of the syngas is either blended by side stream 58 as part of product fuel gas or converted to hydrogen rich gas for feed to dissolver 22.

The vapor stream from stripper 30 is passed by line 40 after partial cooling in heat exchanger 20 to a first liquid recovery system 42.

There, through a plurality of separators 44 operating in connection wherein with sundry cooling and scrubbing operations, gaseous feed is reduced to a temperature consonant for recovery of the liquid hydrocarbon solvent. Separated with the liquid hydrocarbon solvent having a boiling point up to 750° F, preferably from about 300° to about 750° F, and preferably from about 500° to 750° F, are residual carryover solids from the stripper 30. The condensate from each separator 44 employed is passed by lines 46 for combination in line 48. The combined liquid hydrocarbon solvent and collected solids are passed by line 16 to slurry mixer 14 or solvent storage (not shown).

The vapor effluent after first cooling to approximately 150° F is passed to light liquid hydrocarbon separator 50. The light liquid hydrocarbon condensate formed contains, with some overlap, $C_5$ hydrocarbons up to the boiling point of the hydrocarbons recovered in separator system 42, e.g., up to about 800° F, preferably up to about 500° F, more preferably up to 300° F. The light liquid hydrocarbon from separator 50 may be recovered as liquid fuel or transferred by line 52 with combined hydrogen rich gas formed from a minor portion of the syngas from gasifier 26 to hydrotreater 54.

As indicated, a hydrogen rich gas may be formed from a portion of the gasifier effluent in line 56, which contains from about 5 to 50% hydrogen, to the extent gasifier product is not withdrawn by line 58 as product fuel gas. The syngas in line 56 is passed to separator 60 and then to separator 62 through a venturi scrubber where any solids and any unconverted hydrocarbons present are removed from the gas stream and returned to line 16 for recycling to mixer 14. The effluent from separator 62 is passed by line 64 to heat exchanger 68 where the gas is raised to a temperature at which it will undergo a catalytic water gas shift and to shift converter 66 where the hydrogen content of the reaction is increased. The effluent of shift converter 66 after being cooled in exchanger 68 and air cooler 70 passes through separator 72 and through absorber 74 where it is stripped of at least a portion of the contained carbon dioxide in a manner well known in the art.

The hydrogen rich effluent of absorber 74 is split. A portion is combined with the light liquid hydrocarbon in line 52 and passed from line 52 after heat exchange with the effluent of hydrotreater 54 in exchanger 76 to hydrotreater 54. Fired heater 76 serves for start up and to the extent required as a supplemental heater.

Processing in hydrotreater 54 serves to release the bound sulfur from the light liquid hydrocarbon as hydrogen sulfide. Conversion normally occurs in the presence of a hydrotreating catalyst with the temperature and pressure being dictated by the severity of treatment required to cleave the carbon sulfur bonds.

The effluent from hydrotreater 54 is passed by line 78 to hydrogen sulfide stripper 80 where it is combined with the balance of the hydrogen rich gas in line 82 from carbon dioxide absorber 74. In hydrogen sulfide stripper 80 hydrogen rich gas carries off the released hydrogen sulfide. The hydrogen rich gas may be returned in line 84 as the source of hydrogen to line 24 for feed to dissolver 22. In the alternative or in combination, a portion of the vapor effluent of light liquid hydrocarbon separator 50 may be provided by line 86 as the source of hydrogen in dissolver 22. Another alternative is simply to purge the hydrogen sulfide-hydrogen mixture from stripper 80.

The treated light hydrocarbon oil substantially free of hydrogen sulfide is passed by line 88 for combination with a part of a purified vapor stream from separator 50 and passed to reformer 90. For purification, the vapor effluent from separator 50 is passed by line 92 to acid gas scrubber 94 for removal of hydrogen sulfide and carbon dioxide.

The effluent from absorber 94 is split. A portion is passed to a first methanator in stage 96 operated at an inlet temperature above about 900° F with an outlet temperature of up to about 1500° F. The first stage methanator 96 contains at least one metal of the third period of Group VIII of the Periodic Table as published as the "Periodic Table with Atomic Weights," in *Chemical Engineers' Handbook,* Perry, McGraw-Hill Book Company, Inc., 1950, incorporated herein for reference, such as nickel, cobalt, iron deposited on a temperature stabilized, ceramic alumina support. Methanation occurs in the presence of steam for carbon control as described in U.S. Pat. No. 3,938,968 issued to two of the instant inventors and incorporated herein by reference.

The exotherm of the high temperature effluent of methanator 96 provides the heat to account for the endothermic reaction which occurs in reformer 90.

The balance of the effluent from absorber 94 which comprises hydrocarbons containing up to about 5 carbon atoms, hydrogen and carbon monoxide, is passed by line 98 to line 88 where it is combined with the light hydrocarbons and added after further heating in heater 100 to reformer 90. Reformer 90 operates at a temperature from 1200° to 1500° F, in the presence of steam employing a conventional reforming catalyst. Hydrocarbons introduced are reformed in the presence of steam at a temperature from 1200° to 1500° F at system operating pressure to yield methane, hydrogen and the oxides of carbon. Operation in the desired temperature range is assured by the heat supplied from the effluent of the first adiabatic methanator 96.

After cooling the reformer effluent may be passed directly through a series of adiabatic bulk methanators 102 with cooling between each stage to increase the methane content of the gas stream to a desired level. Typically, the bulk methanators 102 are operated as described in U.S. Pat. No. 3,938,968.

Preferably, the gas stream from reformer 90 is passed after cooling through shift convertor 104 containing a catalyst such as a cobalt molybdate catalyst where residual bound sulfur is converted to hydrogen sulfide which is removed in scruber 106. While beneficial to the methanation operation as described in U.S. Pat. No. 3,938,968, this operation is essential where methanation occurs in a conventional manner as described, for instance, in U.S. Pat. No. 3,511,624 to Humphries et al, incorporated herein by reference. In conventional methanation, the catalysts employed are prone to poisoning by hydrogen sulfide. This is not true of the reformer and high temperature methanation catalyst for the methanation system depicted. Such catalysts are sulfur tolerant, and the hydrogen sulfide can reduce steam requirements. Yield may be reduced, however, thus making the use of the shift operation advantageous.

The final effluent of the bulk methanator, typically at a methane content of about 50%, may be passed after water removal in separator 108 to a $CO_2$ removal unit (not shown) to raise the methane content of the gas stream to the level desired for end use application. In addition, dry methanation may also be employed prior to or after $CO_2$ removal, as described in U.S. Pat. No. 3,938,968.

EXAMPLE

Washed coal ground to a particle size less than 200 mesh is passed at a temperature of 100° F to a slurry mixer and combined with a liquid hydrocarbon solvent at a temperature of 353° F, the weight ratio of liquid hydrocarbon solvent to coal being 2 pounds per pound. The resultant slurry at a temperature about 277° F is pumped to a pressure of 1300 psig and preheated in indirect heat exchange with the vapor effluent of a stripper to 650° F for feed to a liquefaction zone operating at a temperature between 820° F and 870° F, and at a pressure of 1175 psig.

A hydrogen rich gas produced from an effluent of a gasification zone is combined with the slurry in a dissolver in an amount slightly in excess of 2% by weight hydrogen based on the weight of coal. The effluent of the liquefaction zone containing vaporized hydrocarbons, liquid hydrocarbons, hydrogen, hydrogen sulfide and a solid residue is passed to a stripping zone operated at 1170 psig, along with a synthesis gas obtained from the gasification zone and entering at a temperature of 1100° F and a pressure of 1175 psig.

The bottoms of the stripper at a temperature of 935° F are passed to a gasification unit operated at 1255 psig where, upon the addition of oxygen and steam, the carbon is essentially completely gasified to carbon dioxide and carbon monoxide with attendant formation of hydrogen.

A major portion of the effluent of the gasification zone is passed to the stripper as stripper gas and the minor portion to production of hydrogen rich gas for the feed to the dissolver.

The vapor effluent of the stripping zone at 857° F contains hydrogen, carbon monoxide, carbon dioxide, hydrogen sulfide and vaporized hydrocarbons. The effluent is first passed to a high pressure separator operated at 1155 psig at a temperature of 346° F, where there is collected a condensate of the liquid hydrocarbon solvent for recycle at a reduced pressure to a storage tank which feeds the slurry tank.

The gaseous effluent from the high pressure separator after cooling is passed to a gas-liquid separator operated at 1145 psig and 120° F where there is formed a light liquid hydrocarbon and a vapor effluent containing hydrogen sulfide, carbon dioxide, carbon monoxide, hydrogen and vaporized hydrocarbons including $C_5$ and less hydrocarbons.

The light liquid hydrocarbon produced from the gas liquid separator is hydrotreated for release of bound sulfur and the hydrogen and contained hydrogen sulfide purged. The stripped and desulfurized liquid hydrocarbon is heated to 900° F for passage to an adiabatic reformer operating at 1100° F.

Simultaneously, the vapor effluent from the liquid separator is treated for removal of hydrogen sulfide, carbonyl sulfide, ammonia and carbon dioxide and passed in part with steam heating to 900° F to a first methanation zone. The catalyst in the methanation zone is one consisting of 16% by weight nickel deposited on a high purity alumina support known as SAHT-99 manufactured and sold by the Carborundum Company. This support has a typical composition of 99.5% by weight $Al_2O_3$; 0.02% by weight $SiO_2$; 0.04% by weight $Fe_2O_3$ and 0.45% by weight $Na_2O$. The surface area is in a range of 0.5 to 5.5 m²/gm.

The effluent of the methanator and another portion of the purified vapor are combined with the purified light liquid hydrocarbon in the adiabatic reformer. The effluent of the reformer after cooling to 700° F is passed to a shift converter containing a cobalt molybdate catalyst. The effluent of the shift converter is cooled and passed to an acid gas removal unit for additional removal of $CO_2$, hydrogen sulfide and COS.

After reheating to 900° F, the gas steam is passed to four methanation zones in series with cooling between each stage of methanation to provide a feed temperature to each stage of 900° F. The catalyst employed in each methanation zone is the same as that employed in the first methanation zone.

After the last stage of methanation, the gas stream is cooled to first condense water and passed to a carbon dioxide separator.

After carbon dioxide separation, the gas stream is passed to a dry methanation stage containing a conventional methanation catalyst where methane content is increased. After final $CO_2$ removal and drying there is provided a synthetic natural gas of higher than 90.0% methane content.

What is claimed is:

1. A process for the production of methane which comprises in combination the steps of:
   a. forming a slurry of particulate coal in a liquid hydrocarbon solvent comprising hydrocarbons boiling up to about 750° F and generated from the liquefaction of coal in the presence of hydrogen;
   b. combining the slurry and a hydrogen containing gas in a liquefaction zone maintained at a temperature from about 700° to about 1000° F and at a pressure up to about 2500 psi for a time sufficient to convert a substantial portion of coal to fluid hydrocarbons and a solid residue of liquefaction;
   c. combining the effluent, fluid hydrocarbons and the solid residue of liquefaction from the liquefaction zone with a synthesis gas in a stripping zone and forming a liquid-solids fraction comprising liquid hydrocarbons boiling above the boiling point of the liquid hydrocarbon solvent and the solid residue of liquefaction and a vapor fraction comprising hydrocarbons, carbon monoxide, carbon dioxide, hydrogen sulfide and hydrogen;
   d. combining, in a gasification zone, the liquid-solids fraction from the stripping zone with steam and oxygen in an amount sufficient to gasify substantially all of the carbon contained in the liquid-solids fraction to generate a synthesis gas comprising hydrogen and the oxides of carbon;
   e. passing a major portion of the synthesis gas to the stripping zone to form the vapor fraction;
   f. separating the vapor fraction by cooling and condensation into a liquid hydrocarbon solvent fraction, a light liquid hydrocarbon fraction and a residual vapor fraction comprising hydrocarbons containing up to about 5 carbon atoms, hydrogen sulfide, carbon dioxide, carbon monoxide and hydrogen;
   g. returning at least a portion of the liquid hydrocarbon solvent fraction to form additional slurry;
   h. converting a minor portion of the synthesis gas from the gasification zone into a hydrogen rich gas stream;
   i. hydrotreating the light liquid hydrocarbon fraction with at least a portion of the hydrogen rich gas stream to convert bound sulfur to hydrogen sulfide and separating the formed hydrogen sulfide from the hydrogen sulfide lean light liquid hydrocarbon;
   j. passing another portion of the hydrogen rich gas stream as at least part of the hydrogen containing gas to the liquefaction zone;
   k. separating at least a portion of the contained carbon dioxide and hydrogen sulfide from the residual vapor fraction to form a carbon dioxide-hydrogen sulfide lean vapor stream;
   l. methanating a portion of the carbon dioxide-hydrogen sulfide lean vapor stream in the presence of steam and a supported catalyst containing from about 5 to about 35% by weight of at least one metal of the third period of Group VII of the Periodic Table on a temperature stabilized, ceramic alumina support in a first methanation zone having an inlet temperature of at least about 900° F and exit temperature up to about 1500° F;
   m. combining, with steam, the effluent of the methanation zone, the balance of the carbon dioxide-hydrogen sulfide lean vapor stream and the hydrogen sulfide lean light liquid hydrocarbon in a catalytic reforming stage where, at a temperature from about 1200° to about 1500° F maintained by the effluent of the methanation stage, hydrocarbons are reformed to yield an effluent gas stream comprising steam, hydrogen, carbon monoxide, carbon dioxide and methane; and
   n. passing the effluent gas stream from the reforming stage to at least one additional methanation stage where the hydrogen and carbon monoxide react to form additional methane.

2. The process of claim 1 in which the effluent of the reforming stage, prior to passage to an additional methanation stage, is
   a. contacted in a shift conversion zone with a catalyst to convert at least a portion of residual bound sulfur contained in the effluent of the reforming stage to hydrogen sulfide, and
   b. treating the shifted gas for separation of at least formed hydrogen sulfide.

3. The process of claim 1 in which the liquid hydrocarbon solvent predominantly comprises hydrocarbons boiling in the range from about 300° to about 750° F.

4. The process of claim 1 in which the liquid hydrocarbon solvent predominantly comprises hydrocarbons boiling in the range from about 500° to about 750° F.

5. The process of claim 3 in which the light liquid hydrocarbon predominantly comprises hydrocarbons containing more than about 5 carbon atoms to hydrocarbons boiling up to about 300° F.

6. The process of claim 4 in which the light liquid hydrocarbon predominantly comprises hydrocarbons containing more than about 5 carbon atoms to hydrocarbons boiling up to about 500° F.

7. The process of claim 1 in which liquefaction occurs at a temperature from about 800° to about 900° F.

8. The process of claim 7 in which liquefaction occurs at a pressure from about 1000 to about 1500 psig.

9. The process of claim 1 in which from about 60 to about 90% of the synthesis gas is passed to the stripping zone.

10. The process of claim 1 in which from about 80 to about 90% of the synthesis gas is passed to the stripping zone.

11. The process of claim 2 in which the hydrogen rich gas is supplied to the liquefaction zone in a quantity to provide at least about 2% by weight of the weight of the coal fed to the liquefaction zone.

12. The process of claim 1 in which the effluent gas from the reforming stage is at least passed through a plurality of methanation stages in series with cooling between each stage, each stage containing a supported catalyst containing from about 5 to about 35% of at least one metal of the third period of Group VIII of the Periodic Table on a temperature stabilized, ceramic alumina support, each methanation stage having an inlet temperature of about 900° F and an outlet temperature up to about 1500° F.

13. The process of claim 2 in which the effluent gas following treatment for hydrogen sulfide removal is at least passed through a plurality of methanation stages in series with cooling between each stage, each stage containing a supported catalyst containing from about 5 to about 35% of at least one metal of the third period of Group VIII of the Periodic Table on a temperature stabilized, ceramic alumina support, each methanation stage having an inlet temperature of about 900° F and an outlet temperature up to about 1500° F.

14. The process of claim 1 in which the weight ratio of the liquid hydrocarbon solvent to coal in the slurry is from about 1:1 to about 3:1.

15. The process of claim 1 in which the weight ratio of the liquid hydrocarbon solvent to coal in the slurry is from about 1.5:1 to about 2.5:1.

16. A process for the production of methane which comprises in combination the steps of:
   a. forming a slurry of particulate coal in a liquid hydrocarbon solvent predominantly comprising hydrocarbons boiling in the range of from about 300° to about 750° F and generated from the liquefaction of coal in the presence of hydrogen, the weight ratio of the liquid hydrocarbon solvent to coal in the slurry being from about 1:1 to about 3:1;
   b. combining the slurry and a hydrogen containing gas in a liquefaction zone maintained at a temperature from about 700° to about 1000° F and at a pressure up to about 2500 psi for a time sufficient to convert a substantial portion of coal to fluid hydrocarbons and a solid residue of liquefaction;
   c. combining the effluent of fluid hydrocarbons and the solid residue of liquefaction from the liquefaction zone with a synthesis gas in a stripping zone and forming a liquid-solids fraction comprising liquid hydrocarbons having a boiling point above the boiling point of the liquid hydrocarbon solvent and the solid residue of liquefaction and a vapor fraction comprising hydrocarbons, carbon monoxide, carbon dioxide, hydrogen sulfide and hydrogen;
   d. combining, in a gasification zone, the liquid-solids fraction from the stripping zone with steam and oxygen in an amount sufficient to gasify substantially all of the carbon contained in the liquid-solids fraction to generate a synthesis gas comprising hydrogen and the oxides of carbon;
   e. passing at least about 60% of the synthesis gas to the stripping zone to form the vapor fraction;
   f. separating the vapor fraction into the liquid hydrocarbon solvent fraction, a light liquid hydrocarbon fraction and a residual vapor fraction comprising hydrocarbons containing up to about 5 carbon atoms, hydrogen sulfide, carbon dioxide, carbon monoxide and hydrogen;
   g. returning at least a portion of the liquid hydrocarbon solvent fraction to form additional slurry;
   h. converting the balance of the synthesis gas from the gasification zone into a hydrogen rich gas stream;
   i. hydrotreating the light liquid hydrocarbon fraction with at least a portion of the hydrogen rich gas stream to convert bound sulfur to hydrogen sulfide and separating the formed hydrogen sulfide to form a hydrogen sulfide lean light liquid hydrocarbon;
   j. passing another portion of the hydrogen sulfide containing hydrogen rich gas stream as at least part of the hydrogen containing gas to the liquefaction zone;
   k. separating at least a portion of the contained carbon dioxide and hydrogen sulfide from the residual vapor fraction to form a carbon dioxide-hydrogen sulfide lean vapor stream;
   l. methanating a portion of the carbon dioxide-hydrogen sulfide lean vapor in the presence of a steam supported catalyst containing from about 5 to about 35% by weight of at least one metal of the third period of Group VIII of the Periodic Table on a temperature stabilized, ceramic alumina support in a first methanation zone having an inlet temperature of at least about 900° F and exit temperature up to about 1500° F;
   m. combining, with steam, the effluent of the methanation zone, the balance of the carbon dioxide-hydrogen sulfide lean vapor stream and the hydrogen sulfide lean light liquid hydrocarbon in a catalytic reforming state where, at a temperature from about 1200° to about 1500° F maintained by effluent of the methanation stage, hydrocarbons are reformed to yield an effluent gas stream comprising steam, hydrogen, carbon monoxide, carbon dioxide and methane; and
   n. passing the effluent gas stream from the reforming stage to at least one additional methanation stage where the hydrogen and carbon monoxide react to form additional methane.

17. The process of claim 16 in which the effluent of the reforming stage, prior to passage to an additional methanation stage is:
   a. contacted in a shift conversion zone with a catalyst to convert at least a portion of residual bound sulfur contained in the effluent of the reforming stage to hydrogen sulfide; and b. treating the shifted gas stream for separation of at least the formed hydrogen sulfide.

18. The process of claim 16 in which the liquid hydrocarbon solvent predominantly comprises hydrocarbons boiling in the range from about 500° to about 750° F.

19. The process of claim 16 in which liquefaction occurs at a temperature from about 800° to about 900° F.

20. The process of claim 16 in which from about 80 to about 90% of the synthesis gas is passed to the stripping zone.

21. The process of claim 16 in which the effluent gas from the reforming stage is at least passed through a plurality of methanation stages in series with cooling between each stage, each stage containing supported catalyst containing from about 5 to about 35% of at least one metal of the third period of Group VIII of the Periodic Table in a temperature stablized, ceramic alumina support, each methanation stage having an inlet temperature of about 900° F and an outlet temperature up to about 1500° F.

22. The process of claim 17 in which the effluent gas following treatment for hydrogen sulfide removal is at least passed through a plurality of methanation stages in series with cooling between each stage, each stage containing supported catalyst containing from about 5 to about 35% of at least one metal of the third period of Group VIII of the Periodic Table in a temperature stabilized, ceramic alumina support, each methanation stage having an inlet temperature of about 900° F and an outlet temperature up to about 1500° F.

23. The process of claim 16 in which the weight ratio of the liquid hydrocarbon solvent to coal in the slurry is from about 1.5:1 to about 2.5:1.

* * * * *

UNITED STATES PATENT OFFICE
CERTIFICATE OF CORRECTION

Patent No. 4,050,908  Dated September 27, 1977

Inventor(s) Gerald P. McNamee et al.

It is certified that error appears in the above-identified patent and that said Letters Patent are hereby corrected as shown below:

Column 2, line 5, " of methane" has been deleted and inserted therefor the paragraph -- Preferably the process is utilized for the production of methane. --.

Column 2, line 35, insert a space after "removal" and before "of". Column 7, line 12, after "steam" insert --after --; line 29, for "steam" should read -- stream ---. Column 8, line 34, for "VII" should read -- VIII --.

Signed and Sealed this

Twenty-first Day of March 1978

[SEAL]

Attest:

RUTH C. MASON
Attesting Officer

LUTRELLE F. PARKER
Acting Commissioner of Patents and Trademarks